US011000646B2

(12) United States Patent
Paoli et al.

(10) Patent No.: US 11,000,646 B2
(45) Date of Patent: May 11, 2021

(54) INFUSION DEVICE FOR ACTING ONTO A TUBE SET

(71) Applicant: Fresenius Vial SAS, Brézins (FR)

(72) Inventors: Mathieu Paoli, Voiron (FR); Damien Archat, Grenoble (FR); Sylvain Petinot, La Mure (FR)

(73) Assignee: Fresenius Vial SAS, Brézins (FR)

( * ) Notice: Subject to any disclaimer, the term of this patent is extended or adjusted under 35 U.S.C. 154(b) by 341 days.

(21) Appl. No.: 15/754,365

(22) PCT Filed: Jul. 14, 2016

(86) PCT No.: PCT/EP2016/066725
§ 371 (c)(1),
(2) Date: Feb. 22, 2018

(87) PCT Pub. No.: WO2017/036652
PCT Pub. Date: Mar. 9, 2017

(65) Prior Publication Data

US 2018/0250468 A1 Sep. 6, 2018

(30) Foreign Application Priority Data

Sep. 1, 2015 (EP) .................................... 15306340

(51) Int. Cl.
*A61M 5/168* (2006.01)

(52) U.S. Cl.
CPC ... *A61M 5/16854* (2013.01); *A61M 2205/332* (2013.01); *A61M 2205/3351* (2013.01);
(Continued)

(58) Field of Classification Search
CPC ...... A61M 5/16854; A61M 2205/3362; A61M 2205/3355; A61M 2205/3351;
(Continued)

(56) References Cited

U.S. PATENT DOCUMENTS

2003/0214412 A1* 11/2003 Ho .................... A61M 5/14228 340/611
2011/0142688 A1 6/2011 Chappel et al.
(Continued)

FOREIGN PATENT DOCUMENTS

CN 102143775 8/2011
WO WO 2004/061399 7/2004

OTHER PUBLICATIONS

International Search Report and Written Opinion, counterpart International Appl. No. PCT/EP2016/066725, dated Sep. 23, 2016 (10 pages).

*Primary Examiner* — Deanna K Hall
(74) *Attorney, Agent, or Firm* — Cook Alex Ltd.

(57) ABSTRACT

An infusion device (1) for acting onto a tube set (2) to transport a medical fluid through the tube set (2) comprises a first housing element (10) constituted to receive a tube section (200, 201) of the tube set (2) and a second housing element (11) being movable with respect to the first housing element (10) such that, in a closed position of the second housing element (11), the first housing element (10) and the second housing element (11) are constituted to receive the tube section (200, 201) in between each other. A sensor device (3) is arranged on the first housing element (10) and having a sensor element (30) for measuring a force on the tube section (200, 201) of the tube set (2). Herein it is provided that the sensor device (3) is arranged on the first housing element (10) in an elastically displaceable manner, wherein the sensor device (3) is supported on the first housing element (10) via at least one spring element (33). In this way an infusion device is obtained which may be less prone to variations in the squeezing of a tube section in between the sensor element and a movable housing element, potentially reducing the effort for calibrating infusion
(Continued)

devices and increasing the reliability of pressure measurements on a tube section.

20 Claims, 4 Drawing Sheets

(52) U.S. Cl.
CPC ............... *A61M 2205/3355* (2013.01); *A61M 2205/3362* (2013.01)

(58) Field of Classification Search
CPC .. A61M 2205/332; A61M 2005/16863; A61M 2005/16868; A61M 2005/16872; A61M 2005/16831
See application file for complete search history.

(56) References Cited

U.S. PATENT DOCUMENTS

2011/0232388 A1 9/2011 Butterfield
2012/0079886 A1 4/2012 Beck et al.
2013/0211323 A1* 8/2013 Lee ....................... F04B 43/082 604/67

* cited by examiner

INFUSION DEVICE FOR ACTING ONTO A TUBE SET

The present application is a U.S. National Stage of PCT International Patent Application No. PCT/EP2016/066725, filed Jul. 14, 2016, which claims priority to EP Application No. 15306340, filed Sep. 1, 2015, both of which are hereby incorporated herein by reference.

The invention relates to an infusion device according to the preamble of claim 1.

An infusion device of this kind serves for acting onto a tube set for transporting a medical fluid through the tube set. An infusion device of this kind may for example be constituted as a peristaltic (volumetric) infusion pump having a peristaltic pump mechanism, which for example may act onto a flexible wall section of a pump module as described for example in US 2012/0207635 A1.

The infusion device comprises a first housing element constituted to receive a tube section of the tube set and a second housing element being movable with respect to the first housing element such that, in a closed position of the second housing element, the first housing element and the second housing element are constituted to receive the tube section in between each other. A sensor device is arranged on the first housing element and comprises a sensor element for measuring a force on the tube section of the tube set.

The first housing element may for example comprise a reception channel for receiving the tube section therein. The second housing element, also called the "door" of the infusion device, in this case may for example be arranged pivotably on the first housing element and may be pivoted towards the first housing element in order to, in the closed position, at least partially cover the reception channel such that the tube section received in the reception channel is held on the first housing element. By means of the second housing element the tube section is pressed against the sensor element of the sensor device such that the sensor element is brought into abutment (directly or indirectly via an intermediate part in the shape of a brace or the like) with the tube section and hence is able to measure a force on the tube section. From the force, then, the value of the pressure inside the tube section can be deduced.

Generally, the pressure in the tube section is directly linked to the force measured by the sensor element according to the relation $$P = \frac{F - F0}{K},$$

wherein P denotes the pressure in the tube section, K represents a constant coefficient and F0 denotes the force applied to the tube section when the relative pressure within the tube section is 0. The coefficients F0 and K herein are directly linked to the geometry of the sensor element and the second housing element bringing the tube section into abutment with the sensor element.

Generally, the parameters K and F0 dependent on the squeezing of the tube section in between the second housing element and the sensor element of the sensor device, wherein the squeezing may vary between different devices and may also change over time due to a wear of the infusion device. Because a small variation of the squeezing dimension of the tube section may produce a comparatively large variation of the parameters K and F0, an individual calibration of infusion devices is required, which may have to be repeated after a certain time in order to ensure a reliable overpressure and/or underpressure detection in the tube section by means of the sensor device.

It is an object of the instant invention to provide an infusion device which may be less prone to variations in the squeezing dimension of a tube section in between the sensor element and the movable, second housing part, potentially reducing the effort required for calibrating infusion devices and increasing the reliability of pressure measurements on a tube section.

This object is achieved by means of an infusion device comprising the features of claim 1.

Accordingly, the sensor device is arranged on the first housing element in an elastically displaceable manner, wherein the sensor device is supported on the first housing element via at least one spring element.

The instant invention is based on the finding that in conventional infusion devices a large number of parts influence the squeezing dimension of a tube section of a tube set when receiving the tube section on an infusion device. By arranging the sensor device in a displaceable fashion on the first housing element it can be achieved that the number of parts influencing in the squeezing dimension of the tube section can be reduced, thus obtaining a squeezing dimension of the tube section received in between the first housing element and the second housing element which is more closely defined and which may be subject to smaller variations.

Generally, the squeezing dimension is defined by the distance in between the sensor element and the movable, second housing element by which the tube section is pressed against the sensor element. The squeezing dimension represents the (deformed) width which the tube section assumes when it is squeezed against the sensor element.

The first housing element, in one embodiment, comprises a reception channel for receiving the tube section of the tube set. The reception channel may for example extend longitudinally on a front face of the first housing element and may have the shape of a groove into which the tube section of the tube set can be inserted. The second housing element, for securing the tube section on the first housing element, in this case can be moved from an opened position, in which the reception channel is accessible such that the tube section can be inserted into the reception channel, into the closed position, in which the second housing element at least partially covers the reception channel and in this way holds the tube section in the reception channel.

The tube section may in particular be received on a front face of the first housing element, the front face extending in a plane spanned by a first direction and a second direction perpendicular to the first direction. Herein, the sensor device beneficially is displaceable with respect to the first housing element along a third direction perpendicular to the first direction and the second direction. The sensor device hence may float to some extent with respect to the first housing element on which it is arranged such that the sensor device may assume a defined position relative to the second housing element when bringing the second housing element into its closed position for securing the tube section on the first housing element.

The third direction may correspond to the direction in which the second housing element can be approached towards the first housing element when bringing the second housing element into the closed position.

In one embodiment, the sensor device comprises an abutment element which, in the closed position of the second housing element, is in abutment with the second housing element. Via the abutment element the sensor device hence assumes a defined position with respect to the second housing element when the second housing element is in its closed position. The abutment element may for example be constituted to receive the tube section such that the tube section is placed in between the sensor element of the sensor device and the second housing element, wherein the relative placement of the sensor element and the second housing element is defined by the abutment of the abutment element on the second housing element. The squeezing in between the sensor element and the second housing element hence takes place in a defined, reproducible fashion subject to limited variations between different infusion devices and between different infusion operations.

The abutment element may for example be supported on a first part of the first housing element via a first spring element, wherein this first spring element elastically pretensions the abutment element with respect to the first housing element in a first tensioning direction. In addition, the abutment element may for example be supported on a second part of the first housing element via a second spring element, wherein the second spring element elastically pretensions the abutment element with respect to the first housing element in a second tensioning direction opposite to the first tensioning direction. By means of the first spring element and the second spring element, hence, the abutment element is held on the first housing element in a spring elastic fashion and thus can elastically be displaced with respect to the first housing element.

The first tensioning direction and the opposite, second tensioning direction herein beneficially are parallel to the third direction perpendicular to the plane of extension of the front face of the infusion device on which the tube section is received. When closing the second housing element (the "door" of the infusion device) the position of the abutment element of the sensor device hence may elastically be adapted such that the abutment element may assume a position in which it is in abutment with the second housing element.

In one embodiment, the sensor device comprises a sensor device housing received in a reception opening of the abutment element. The sensor device housing may for example comprise an electric or electronic circuitry for processing and/or forwarding sensor signals received via the sensor element. The sensor device housing may for example include connectors for connecting the sensor device to an external control circuitry.

In one embodiment, the second spring element may act between the second part of the first housing element and the sensor device housing for tensioning the sensor device housing towards the abutment element in the second tensioning direction. The sensor device housing hence is pressed by means of the second spring element against the abutment element such that the sensor device housing is received in the reception opening of the abutment element and is held in the reception opening by means of the second spring element. In this case the abutment element, via the sensor device housing, is tensioned in the second tensioning direction.

In one embodiment, the abutment element comprises a channel section for receiving the tube section of the tube set. This channel section may for example extend longitudinally on the abutment element and may be aligned with a reception channel on the front face of the infusion device. When the tube section is received on the first housing element, the tube section extends through the channel section of the abutment element and is in abutment with the sensor element such that the sensor element may measure a force exerted on the tube section during operation of the infusion device.

The sensor element of the sensor device may be arranged on the abutment element for example such that it reaches into the channel section of the abutment element. The sensor element contacts the tube section when the tube section is received in between the first housing element and the second housing element in the closed position of the second housing element.

In one particular example, the second housing element is arranged pivotably about a pivoting axis on the first housing element. The second housing element in this case may be pivoted with respect to the first housing element between an opened position and the closed position, wherein in the opened position a tube section of the tube set may for example be arranged in a reception channel on a front face of the first housing element, whereas in the closed position the tube section is held and received in between the first housing element and the second housing element.

The infusion device may for example be constituted as a peristaltic infusion pump which peristaltically acts onto a tube section of a tube set, for example a pump module having a flexible wall section which can be deformed in a peristaltic fashion for transporting a medical fluid through the tube set, as it is described for example in US 2012/0207635 A1.

The idea underlying the invention shall subsequently be described in more detail with regard to the embodiments shown in the figures. Herein, FIG. 1 shows a schematic view of an infusion device in the shape of a peristaltic (volumetric) infusion pump;

Figure 1:
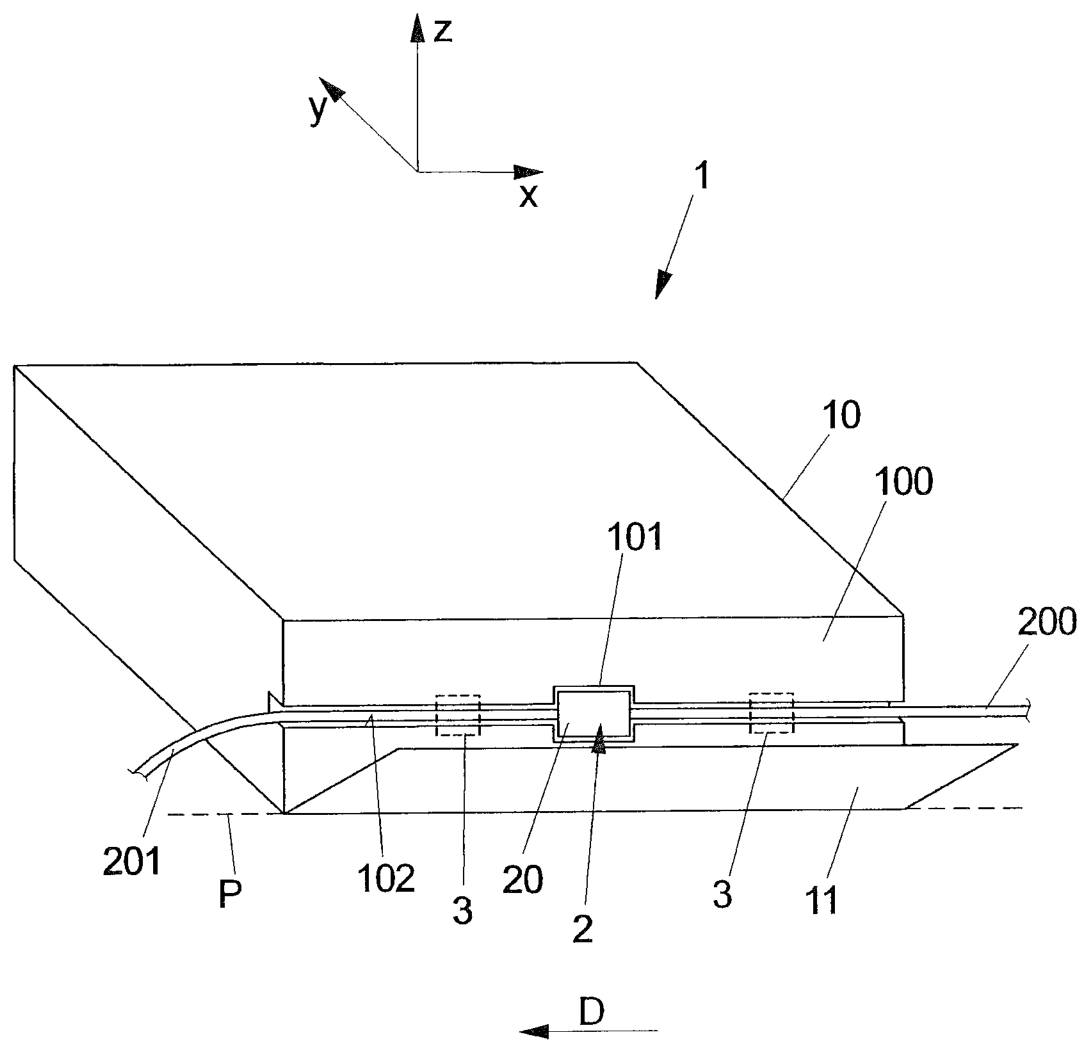

FIG. 1 shows in a schematic view an infusion device 1 in the shape of a peristaltic (volumetric) infusion pump. The infusion device 1 comprises a first housing element in the shape of a housing 10 having a front face 100 and a receptacle 101 arranged on the front face 100. The receptacle 101 is shaped as a reception opening and is constituted to receive a pump module 20 of a (disposable) tube set 2.

Attached to the housing 10 is a second housing element in the shape of a door 11, which is pivotable about a pivoting axis P with respect to the housing 10 for accessing the front face 100 and the receptacle 101 arranged thereon. By pivoting the door 11 away from the front face 100, the receptacle 101 may be accessed for inserting a pump module 2 into the receptacle 101 or for removing the pump module 2 from the receptacle 101. During operation of the infusion device 1, the door 11 is closed such that the tube set 2 is securely held on the housing 10.

On the front face 100 of the housing 10 of the infusion device 1 a reception channel 102 in the shape of a groove is arranged. The reception channel 102 extends longitudinally on the front face 100 and is constituted to receive tube sections 200, 201 extending from the pump module 20 of the tube set 2. If the door 11 is opened, as schematically depicted in FIG. 1, the tube set 2 with its pump module 20 and the tube sections 200, 201 can be attached to the front face 100 of the housing 10 of the infusion device 1 in that the pump module 20 is arranged in the receptacle 101 and the tube sections 200, 201 are placed in the reception channel 102.

By closing the door 11 the tube set 2 can be secured on the front face 100 such that the tube set 2 is held on the infusion device 1.

In the region of the receptacle 101, for example at a bottom face of the receptacle 101, a peristaltic pump mechanism is arranged which is constituted to act onto the pump module 20 for pumping a fluid through the tube set 2 for administering the fluid for example to a patient. The pump mechanism may for example comprise a wobbling device constituted to perform a wobbling action on a flexible wall section, for example a membrane, of the pump module 20 for pumping the medical fluid in a pumping direction D through the pump module 20.

During a pumping operation of the infusion device 1 it shall be detected whether an abnormal pressure condition within the tube set 2 exists, for example due to an occlusion downstream of the pump module 2 or due to an empty-bag condition in a bag supplying medical fluid upstream of the pump module 20. For this, sensor devices 3 may be arranged downstream of the receptacle 101 and upstream of the receptacle 101 for measuring a pressure within the tube sections 201, 200 downstream of the receptacle 101 and upstream of the receptacle 101.

A sensor device 3 downstream of the receptacle 101 may in particular be constituted to detect an overpressure condition (an excessively rising pressure) in the downstream tube section 201. Such overpressure may be due to an occlusion in the downstream tube section 201 and may be hazardous to a patient if for example a continuous infusion at a constant flow rate is required.

The sensor device 3 generally is constituted as a force sensor for measuring a force on the corresponding tube section 200, 201. From the force measured on the tube section 200, 201 a pressure value for the pressure inside the tube can be deduced according to the following equation:

$$P = \frac{F - F0}{K},$$

Herein, P denotes the pressure inside the tube, F denotes the measured force, F0 denotes the force applied to the tube section when the relative pressure within the tube section 200, 201 is 0, and K denotes a constant coefficient.

Figure 2:
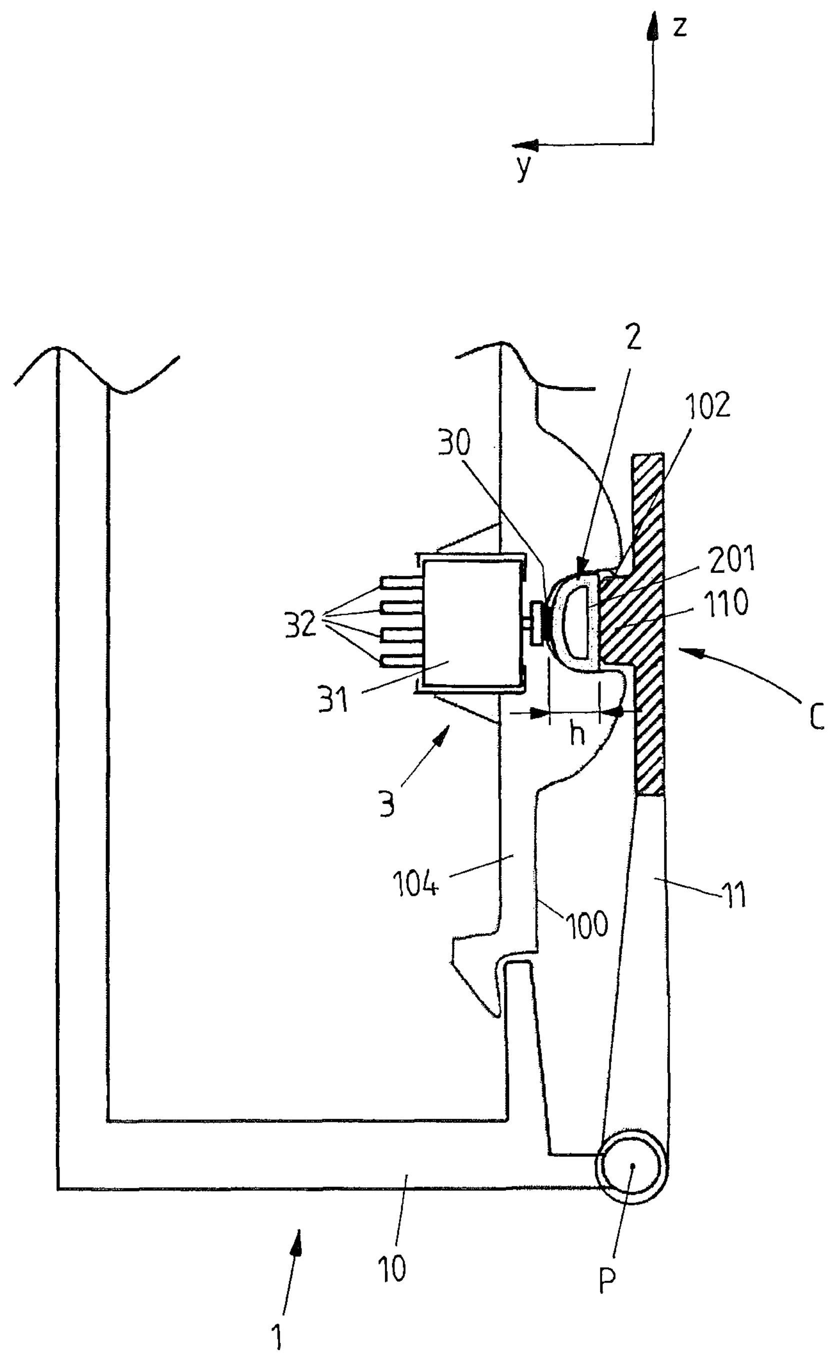
FIG. 2 shows a schematic drawing of an infusion device according to the prior art.

FIG. 2 shows a schematic drawing of a conventional infusion device 1 comprising a sensor device 3 in the shape of a force sensor having a sensor element 30 reaching into a reception channel 102 on a housing element 104 forming the front face 100 of the housing 10 of the infusion device 1. The sensor device 3 comprises a sensor device housing 31 which for example may enclose an electric or electronic circuitry for processing and/or forwarding sensor signals received from the sensor element 30. To the sensor device housing 31 connectors 32 are connected, which serve to provide a connection to for example a control circuitry of the infusion device 1 or the like.

In the example of FIG. 2, a tube section 201 of a tube set 2 is received in the reception channel 102 and, by means of a squeezing section 110 of the door 11, is squeezed into the reception channel 102 such that it is pressed into abutment with the sensor element 30 of the sensor device 3, enabling the sensor device 3 to measure a force on the tube section 201 via the sensor element 30.

The squeezing of the tube section 201 in the reception channel 102 can be described by a squeezing dimension h as indicated in FIG. 2. Generally, the coefficients K and F0 as present in the above-noted equation will depend on this squeezing dimension h, wherein small variations of the squeezing dimension h may have a rather large influence on the coefficients K, F0. Because the squeezing dimension h may depend for example on the reception channel 102 and its shape, the placement of the door 11, the placement of the sensor device 3 and the placement of the housing element 104 with respect to other housing elements of the housing 10, the squeezing dimension h may be different between different infusion devices 1 and may also change over the lifetime of a particular infusion device 1 due to a wear and tear of parts of the infusion device 1.

Figure 3:
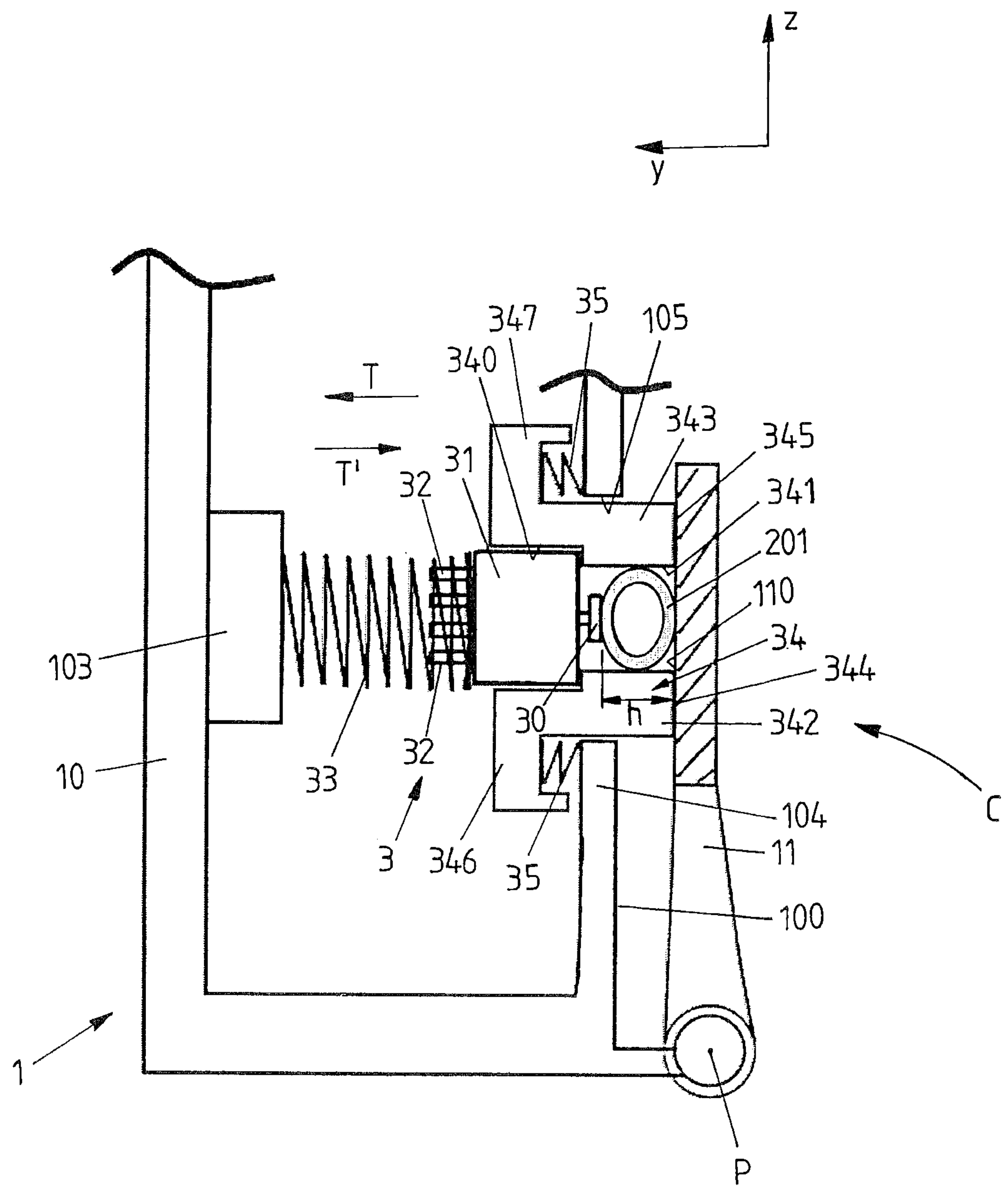
FIG. 3 shows a schematic drawing of an infusion device implementing an embodiment of the instant invention.

FIG. 3 shows an embodiment of the instant invention. In this embodiment the sensor device 3 is placed on the housing 10 in a floating fashion in that it is elastically displaceable along a direction Y perpendicular to the front face 100 (extending in a plane spanned by directions X, Z) of the housing 10.

Figure 4:
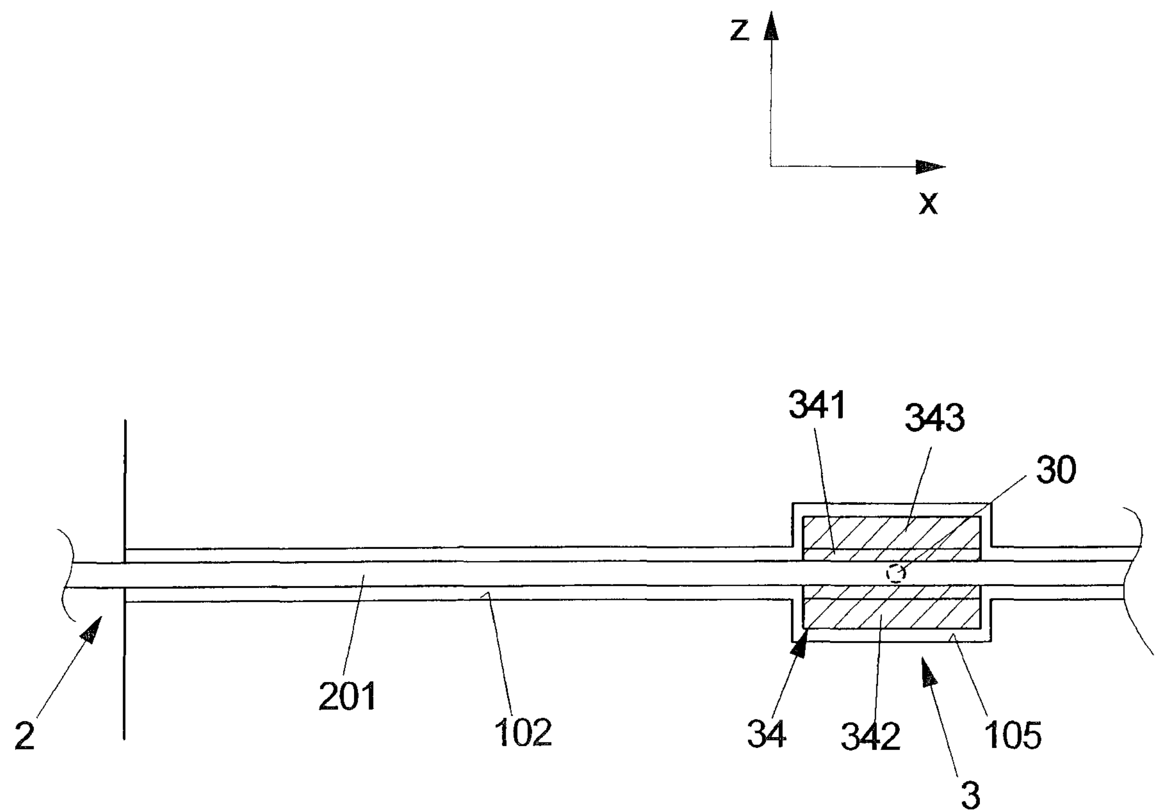
FIG. 4 shows another schematic drawing of the infusion device.

The sensor device 3 comprises an abutment element 34 which comprises a reception opening 340 constituted to receive the sensor device housing 31. The abutment element 34 further comprises two wall sections 342, 343 reaching through an opening 105 of the front housing element 104 forming the front face 100. The wall sections 342, 343 form a channel section 341 in between them, the channel section 341—as illustrated in FIG. 4—being aligned with the reception channel 102 on the front face 100 and being constituted to receive a tube section 200, 201 of a tube set 2.

The opening 105, in one embodiment, can be sealed by a flexible, soft membrane extending in between the wall section 342, 343 and the adjacent edge of the front face 100. The membrane herein is constituted such that the abutment element 34 can freely move horizontally within the opening 105 (along a tensioning direction T), but seals the inside of the housing 10 towards the outside such that moisture and dirt cannot enter into the housing 10.

The abutment element 34 is arranged such that it abuts, via abutment faces 344, 345 on the wall sections 342, 343, a section 110 of the door 11 when the door 11 is closed, as it is shown in FIG. 3. The abutment element 34 hence assumes a defined position relative to the door 11 when the door 11 is closed. Because the sensor device housing 31 and the sensor element 30 have a defined position within the abutment element 34, the squeezing dimension h in between the section 110 of the door 11 and the sensor element 30 is closely defined and subject to only little variations, such that the need for calibrations may at least be reduced and the reliability of a force measurement on a tube section 200, 201 of a tube set 2 may be increased.

The spring elements 35, in one embodiment, are integrally formed with the abutment element 34 for example from plastics. The spring elements 35 primarily serve to ease the assembly of the abutment element 34 in order to position the abutment element 34 within the housing 10.

The spring elements 35 in principle are not necessary for the functioning of the device and may be dispensable.

The abutment element 34, via flange sections 346, 347, is elastically supported on the housing element 104 by means of spring elements 35. In addition, the sensor device housing 31 is supported on a rear housing element 103 by means of another spring element 33. By means of the spring elements 33, 35 the sensor device 3 hence is elastically held in position within the housing 10, wherein the spring elements 35 provide a tension in a tensioning direction T towards the rear housing element 103, whereas the spring element 33 provides an opposite tension in an opposite tensioning direction T' towards the front housing element 104.

To bring the infusion device 1 into an operational state a tube set 2 is inserted with its tube sections 200, 201 into the reception channel 102 on the front face 100 of the infusion device 1. By closing the door 11 (in a closing direction C) the tube set 2 is secured in its position on the front face 100 in that the door 11 covers the reception channel 102 towards the outside.

When closing the door 11 in the closing direction C, the abutment element 34 of the sensor device 3 assumes a position in which it is in abutment with the door 11, wherein the abutment device 34 can elastically be adapted in its position relative to the front face 100 dependent on the position of the door 11 relative to the front face 100. Because the position of the abutment element 34 relative to the door 11 is defined, also the squeezing dimension h is defined and subject to only little variations.

The idea underlying the invention is not limited to the embodiments described above, but may be implemented also in an entirely different fashion.

In particular, the infusion device may be of any sort in which a pressure shall be measured within a tube section of a tube set. A force sensor herein may be used upstream of a pump mechanism and/or downstream of a pump mechanism. The force sensor may have any desired constitution and may for example be constituted by a piezoelectric sensor or the like.

The tube set may be disposable, but does not have to be.

LIST OF REFERENCE NUMERALS

1 Infusion device
10 Housing element
100 Front face
101 Receptacle
102 Reception channel
103 Housing element
104 Housing element
105 Opening
11 Door
110 Squeezing section
2 Tube set
20 Pump module
200 Tube section (inlet)
201 Tube section (outlet)
3 Sensor device
30 Sensor element
31 Sensor device housing
32 Connector
33 Spring element
34 Abutment element
340 Reception opening
341 Channel section
342, 343 Wall section
344, 345 Abutment face
346, 347 Flange element
35 Spring element
C Closing direction
D Pumping direction
h Squeezing dimension
P Pivoting axis
T, T' Tensioning direction
X, Y, Z Direction

The invention claimed is:

1. An infusion device for acting onto a tube set to transport a medical fluid through the tube set, comprising:

a first housing element configured to receive a tube section of the tube set, a second housing element being movable with respect to the first housing element such that, in a closed position of the second housing element, the first housing element and the second housing element are configured to receive the tube section in between each other, and a sensor device arranged on the first housing element and having a sensor element for measuring a force on the tube section of the tube set, wherein the sensor device is arranged on the first housing element in an elastically displaceable manner, wherein the sensor device is supported on the first housing element via at least one spring element, wherein the sensor device comprises an abutment element which, in the closed position of the second housing element, is in direct abutment with the second housing element.

2. The infusion device according to claim 1, wherein the first housing element comprises a reception channel for receiving the tube section of the tube set, and the second housing element in the closed position at least partially covers the reception channel for holding the tube section of the tube set.

3. The infusion device according to claim 1, wherein the first housing element is configured to receive the tube section on a front face of the first housing element, the front face extending in a plane spanned by a first direction and a second direction perpendicular to the first direction.

4. The infusion device according to claim 3, wherein the sensor device is displaceable, with respect to the first housing element, along a third direction perpendicular to the first direction and the second direction.

5. The infusion device according to claim 1, wherein the abutment element is supported on a first part of the first housing element via a first spring element, wherein the first spring element elastically pretensions the abutment element with respect to the first housing element in a first tensioning direction.

6. The infusion device according to claim 5, wherein the abutment element is supported on a second part of the first housing element via a second spring element, wherein the second spring element elastically pretensions the abutment element with respect to the first housing element in a second tensioning direction opposite to the first tensioning direction.

7. The infusion device according to claim 5, wherein the sensor device comprises a sensor device housing received in a reception opening of the abutment element, wherein the first spring element acts between the first part of the first housing element and the sensor device housing for tensioning the sensor device housing towards the abutment element in the first tensioning direction.

8. The infusion device according to claim 1, wherein the abutment element comprises a channel section for receiving the tube section of the tube set.

9. The infusion device according to claim 8, wherein the sensor element of the sensor device reaches into the channel section and is configured to contact the tube section when the tube section is received in between the first housing element and the second housing element in the closed position of the second housing element.

10. The infusion device according to claim 1, wherein the second housing element is pivotable about a pivoting axis with respect to the first housing element.

11. The infusion device according to claim 1, wherein the infusion device defines a peristaltic infusion pump for peristaltically acting onto the tube section of the tube set for transporting a medical fluid through the tube set.

12. An infusion device for acting onto a tube set to transport a medical fluid through the tube set, comprising:

a first housing element configured to receive a tube section of the tube set, a second housing element being movable with respect to the first housing element such that, in a closed position of the second housing element, the first housing element and the second housing element are configured to receive the tube section in between each other, and a sensor device arranged on the first housing element and having a sensor element for measuring a force on the tube section of the tube set, wherein the sensor device is arranged on the first housing element in an elastically displaceable manner, wherein the sensor device is supported on the first housing element via at least one spring element, wherein the sensor device comprises an abutment element having first and second wall sections with a channel section therebetween, the first and second wall sections, in the closed position of the second housing element, being in direct abutment with the second housing element, and the channel section being configured to receive the tube section therein.

13. The infusion device according to claim 12, wherein the abutment element has a reception opening formed in the channel section configured to receive the sensor element, the abutment element thus being supported on a first part of the first housing element via the at least one spring element.

14. The infusion device according to claim 13, wherein the abutment element is supported on a second part of the first housing element via at least one additional spring element, wherein the at least one additional spring element elastically pretensions the abutment element in a tensioning direction opposite a tensioning direction of the at least one spring element.

15. The infusion device according to claim 12, wherein the first housing element comprises a reception channel for receiving the tube section of the tube set, and the second housing element in the closed position at least partially covers the reception channel for holding the tube section of the tube set.

16. The infusion device according to claim 12, wherein the first housing element is configured to receive the tube section on a front face of the first housing element, the front face extending in a plane spanned by a first direction and a second direction perpendicular to the first direction, and the sensor device is displaceable, with respect to the first housing element, along a third direction perpendicular to the first direction and the second direction.

17. The infusion device according to claim 12, wherein the sensor device comprises a sensor device housing received in a reception opening of the abutment element, wherein the at least one spring element acts between the first part of the first housing element and the sensor device housing for tensioning the sensor device housing towards the abutment element in a tensioning direction.

18. The infusion device according to claim 12, wherein the sensor element of the sensor device reaches into the channel section and is configured to contact the tube section when the tube section is received in between the first housing element and the second housing element in the closed position of the second housing element.

19. The infusion device according to claim 12, wherein the second housing element is pivotable about a pivoting axis with respect to the first housing element.

20. The infusion device according to claim 12, wherein the infusion device defines a peristaltic infusion pump for peristaltically acting onto the tube section of the tube set for transporting a medical fluid through the tube set.

* * * * *